US005748749A

United States Patent [19]

Miller et al.

[11] Patent Number: 5,748,749

[45] Date of Patent: May 5, 1998

[54] ACTIVE NOISE CANCELLING MUFFLER

[75] Inventors: Scott Miller, Baltimore; J. Clay Shipps, Catonsville, both of Md.

[73] Assignee: Noise Cancellation Technologies, Inc., Linthicum, Md.

[21] Appl. No.: 670,111

[22] Filed: Jun. 25, 1996

Related U.S. Application Data

[63] Continuation-in-part of Ser. No. 240,429, May 10, 1994, abandoned, which is a continuation-in-part of Ser. No. 37,755, Mar. 24, 1993, abandoned.

[51] Int. Cl.$^6$ ............................ A61F 11/06; H03B 29/00

[52] U.S. Cl. ........................................ 381/71.5; 381/71.7

[58] Field of Search .............................. 381/71, 94, 71.1, 381/71.5, 71.7, 71.2, 94.1; 181/206

[56] References Cited

U.S. PATENT DOCUMENTS

| | | | |
|---|---|---|---|
| 4,527,282 | 7/1985 | Chaplin et al. | 381/71.5 |
| 5,044,464 | 9/1991 | Bremigan | 381/71.5 |

OTHER PUBLICATIONS

Kido et al., "A New Arrangement of Additional Sound Source in an Active Noise Control System", Inter–Noise 89, Dec. 4–6 1989, pp. 483–488.

*Primary Examiner*—Curtis Kuntz
*Assistant Examiner*—Ping W. Lee

[57] ABSTRACT

An active muffler noise cancellation system having an active controller, a speaker housing with acoustic compliance spaces, a duct extension in communication with said speaker housing and adapted to conform a dipole radiation pattern into a plane wave which can be measured by a microphone.

13 Claims, 7 Drawing Sheets

ACTIVE NOISE CANCELLING MUFFLER

This application is a continuation-in-part of U.S. patent application Ser. No. 08/240,429, filed May 10, 1994, and entitled "Active Noise Cancelling Muffler", now abandoned which is a continuation-in-part of U.S. patent application Ser. No. 08/037,755 filed Mar. 24, 1993 now abandoned.

BACKGROUND OF THE INVENTION

In implementing a muffler system which relies on active cancellation of the offensive noise source, problems of packaging and durability are critical. Other authors have described arrangements which permit high acoustical outputs over a predetermined frequency range in a relatively small package, for example, U.S. Pat. No. 5,097,923 and PCT/US91/02731, "Improvements In and Relating to Transmission Line Loudspeakers" to Hoge et al. "Hoge '731")

Several authors have described devices which cancel noise propagating through a pipe or duct. For example, Chaplin in U.S. Pat. No. 4,122,303 and Kato in U.S. Pat. No. 4,805,733 propose the use of undefined noise sources placed within the duct to cause a reflection of the propagated sound. Other authors, for example, Eriksson in U.S. Pat. No. 4,665,549 and Angelini et al in U.S. Pat. No. 4,177,874 and Bremigan in U.S. Pat. No. 5,044,464 define the device being inserted into the duct. A refinement in these systems is represented by the devices described by Ziegler et al in U.S. Pat. No. 5,094,923 ("Ziegler '923") and Hoge '731, both of which are herein incorporated by reference. These patents and applications describe piping systems in which the active control anti-noise source is placed concentric to the duct and in the plane of the duct outlet. The active anti-noise source described in both cases is a tuned acoustic enclosure which emits high power sound throughout a limited frequency band. The sound output per unit volume is maximized through the use of this type of source. Using this type of outlet configuration, the highest possible frequency can be canceled with the anti-noise source and many of the environmental problems associated with placing a transducer in a corrosive gas flow are avoided almost entirely.

The use of noise sources which are placed in close proximity to the outlet of a pipe has been cited extensively in the technical literature. For example, Chaplin in U.S. Pat. No. 4,489,441 and Nelson and Elliott, *Active Control of Sound*, 1992, pp. 233–244 describe this arrangement. Kido et al in "A New Arrangement of Additional Sound Source in an Active Noise Control System" from *Proceedings of Internoise* '89, Dec. 1989, pp. 483–488, and Hall et al in "Active Control of Radiated Sound from Ducts", *ASME Transactions Journal of Vibration and Acoustics*, July 1992, pp. 338–346 describe several different pipe outlet configurations. However, these authors propose the use of a very simple acoustic source or make no mention of the type of active transducer to be used.

Attempts to use active anti-noise sources on mufflers or other applications involving an exhaust pipe, include the work of Cain, U.S. Pat. No. 5,272,286, which shows an active noise cancelling device surrounding an exhaust pipe in a generally concentric configuration. The problem with such an arrangement is the tremendous expense involved in building something in direct contact with a hot exhaust pipe, the inability to retrofit the system to existing tailpipes and its enormous bulk as well as other problems in its operation. A similar device is shown in Japanese Application, 60-22010, entitled "Exhaust Noise Reducing Device" by Toshiyuki Kaminaga, published on Feb. 4, 1985. Scherrer, in French Patent No. 1,190,317, published Oct. 12, 1959 shows a system very much like Cain, supra, where concentric pipes empty into a mixing chamber. Finally, U.S. Pat. No. 4,487,289, Dec. 11, 1984, entitled "Exhaust Muffler with Protective Shield", shows an extension fitting over a tailpipe, again like Cain.

None of these patents or applications provides the important advantages of the present invention. The current invention seeks to add enhancements which improve the packagability and durability of active muffler devices while improving their performance. The importance of durability and low cost in such systems cannot be overstated. Passive devices which represent the current state of the art are inexpensive and very durable, sometimes performing for decades without attention of any kind. Therefore, it is essential to utilize the lowest cost, most durable system to enhance the operation of active systems.

SUMMARY OF THE INVENTION

The invention relates to the enhancement of active acoustical attenuation by coupling an engine exhaust pipe with the acoustic exhaust of an active enclosure. The active enclosure uses active cancellation, i.e., a secondary noise source, interfering destructively with the original source, such that a reduction in noise is achieved.

When active noise control is applied to an offending noise source, a secondary source is placed in close proximity to the offensive noise source. The secondary source can be placed either around the offensive noise source, concentrically, or beside the noise source, in a dipole configuration, as long as the separation between the two source centers is much smaller than the wavelength of the highest frequency of cancellation. The secondary source creates an acoustic wave form equal in amplitude and 180 degrees out of phase from the offensive source. The secondary source is driven by an adaptive controller system that requires a feedback microphone. The feedback microphone measures the effectiveness of the destructive interference and is used to adjust the signal of the secondary source and optimize cancellation.

Preferably, a duct extension is fitted over the end of both the engine exhaust pipe and the acoustic port. The secondary source in this invention is similar to those mentioned in the prior art, but is connected via a port, usually the same size or slightly larger than the exhaust pipe, to an extension duct. As will be pointed out in greater detail below, the duct extension of this invention provides important advantages, all of which act to improve the performance of the system.

The control system for the invention may use the sync control described in U.S. Pat. No. 4,490,841 to Chaplin, the control described in U.S. Pat. No. 5,105,377 to Ziegler or that described in co-pending PCT Application Serial No. PCT/US92/05228, entitled, "Control System Using Harmonic Filters". All these control systems use a residual microphone and a sync to an engine or motor. The control system also may use the digital virtual earth/adaptive feedforward system described in co-pending U.S. patent application Ser. No. 08/188,869, entitled "Adaptive Feedforward and Feedback Control System". In such a case, no sync is required but a second microphone is used to sense the exhaust noise upstream. All four of the patents/applications are herein incorporated by reference.

In general this invention provides improved coupling between a dipole oriented engine exhaust and an active enclosure acoustic port. The invention increases the amount of attenuation achievable with a dipole oriented engine exhaust and an active enclosure acoustic port and decreases the amount of power required to achieve a certain amount of attenuation for a given active noise cancellation system.

It also allows for the acoustic port of the active enclosure to be shorter thereby increasing the acoustic output of the active enclosure and allows for surface mounting of an error sensor. The arrangement provides protection to the error sensor from road debris, provides a way to integrate the error sensor cable into the active enclosure to minimize cable and protects the cable by encasing it in a conduit. The arrangement may incorporate a heat shield to protect the error sensor or sensing microphone. The duct extension can be styled in a variety of shapes.

Accordingly, it is an object of this invention to provide improved coupling between a dipole oriented engine exhaust and an active enclosure acoustic port.

Another object of this invention is to increase the amount of attenuation achievable with a dipole oriented engine exhaust and active enclosure acoustic port.

A further object of this invention is to decrease the amount of power required to achieve a certain amount of attenuation for a given active noise cancellation system in a dipole orientation.

A still further object of this invention is to allow the active enclosure to be mounted further from the vehicle bumper and behind the automobile muffler and further from the road surface.

Yet another object of this invention is to provide a channel which will allow harmful engine exhaust gases to exit out from underneath the vehicle at the regulatory distance.

Additional objects of the invention include:

(i) allowing the acoustic port of the active enclosure to be shorter thereby increasing the acoustic output of the active enclosure;

(ii) allowing a surface for mounting the error sensor;

(iii) providing protection to the error sensor from road debris and foreign matter;

(iv) providing a way to integrate the error sensor cable into the active enclosure so that the active enclosure and the error sensor may be powered from one input cable;

(v) providing protection to the error sensor cable by enclosing the cable in a built in conduit which mates with the active enclosure; and (vi) providing an internal heat shield to protect the error sensor from extreme exhaust gas temperatures.

These and other objects will become apparent when reference is had to the accompanying drawings and the detailed description below.

DESCRIPTION OF THE INVENTION

Figure 1:
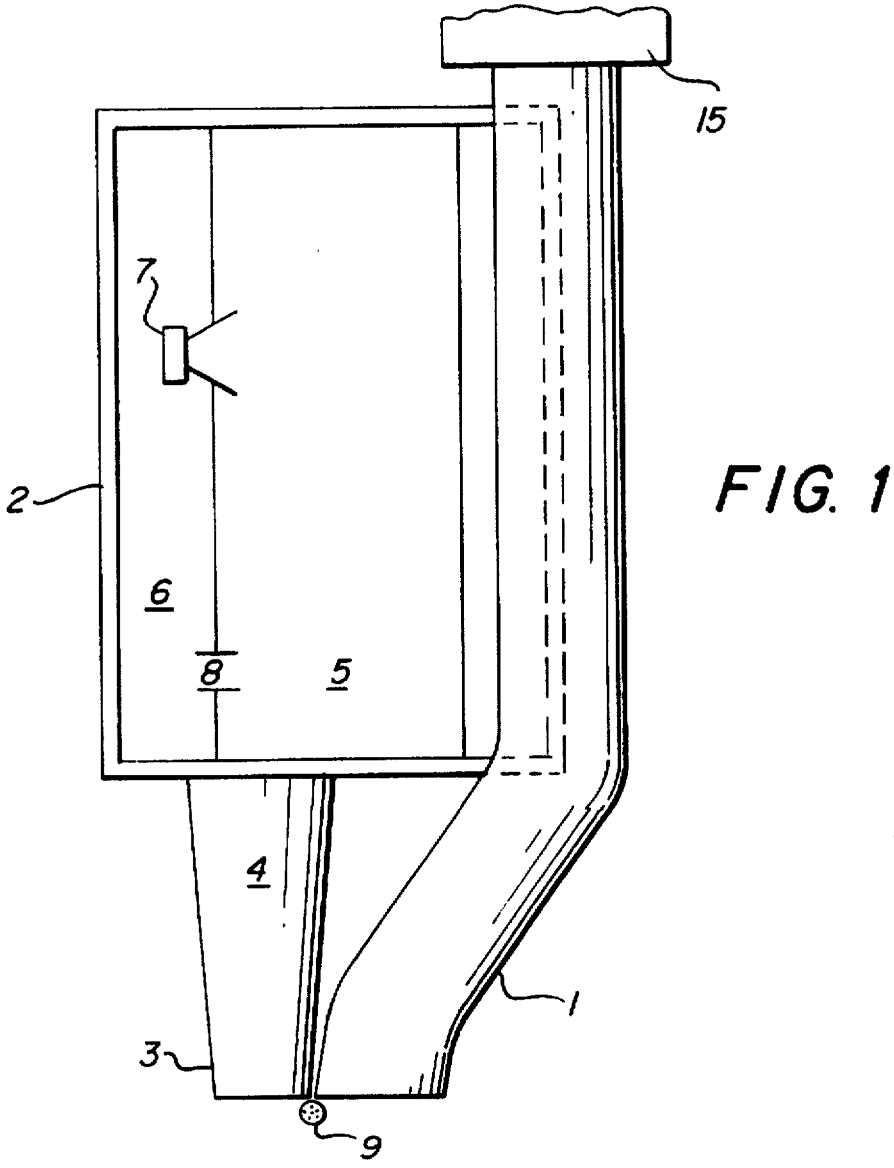
FIG. 1 is a plan view of the preferred embodiment of this invention.

This invention utilizes basic configurations similar to those described in Ziegler '923 and Hoge '731 as described above. The instant device, however, instead of being arranged concentric with the pipe, as in the prior art, is non-integral with the pipe as shown in FIG. 1. An anti-noise source or active transducer means (secondary source) 2 is placed such that the outlet 3 is placed near the outlet of pipe 1 connected to passive muffler 15 which contains a flow of gas containing pressure pulsations.

Passive muffler 15 is used to reduce noise at frequencies above the capability of the active anti-noise source 2. Active anti-noise source 2 consists of outlet acoustic mass 4, acoustic compliances 5 and 6, speaker driver 7, and optionally, an acoustic mass 8.

Figure 2:
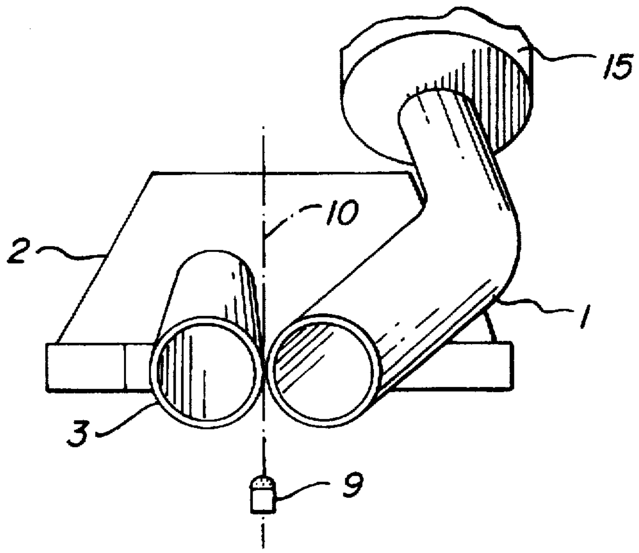
FIG. 2 is a plan view of the embodiment of FIG. 1.
Figure 3:
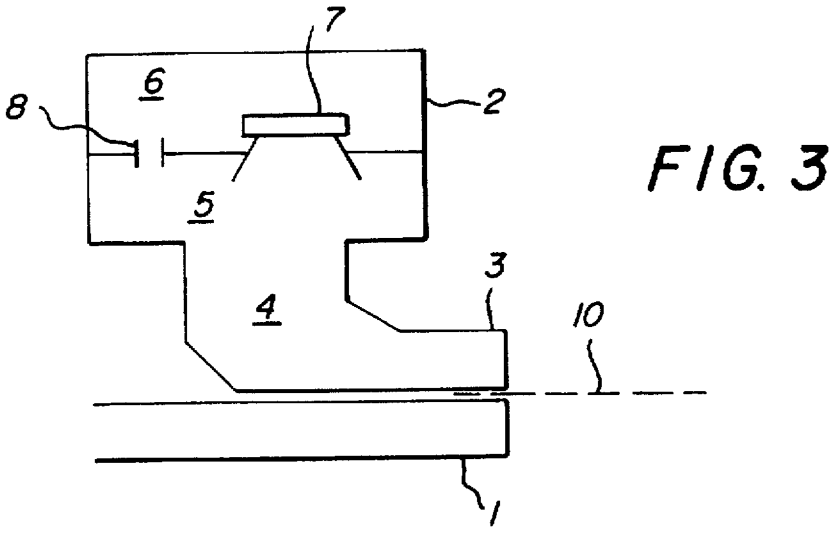
FIG. 3 is an alternative embodiment of the muffler system of this invention.
Figure 4:
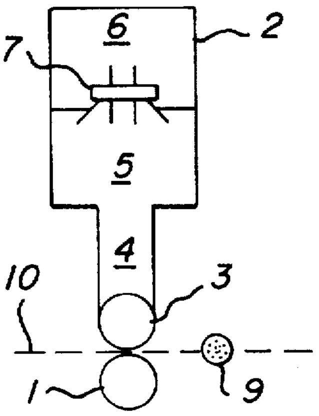
FIG. 4 is an end view of the muffler system of FIG. 3 showing its relationship to a tailpipe.

FIG. 2 shows the two outlets 1 and 3 from the end. If a microphone 9 is placed on the plane 10 between the pipe 1 and the active source outlet 3, an electronic controller outlet (FIG. 9) connected to the microphone will cause the two sources to form an acoustic dipole. A dipole has a directional radiation pattern, but if the acoustic centers of the two sources are within approximately one tenth of a wavelength the minimum cancellation will be approximately 10 decibels. This minimum will occur along the line through the centers of the source outlet 1 and anti-noise source outlet 3. For this reason, it is sometimes advantageous to orient the two sources above and below each other, as shown in FIGS. 3 and 4, since microphones or listeners are less likely to be located above or below the sources if the device is mounted on a vehicle. However, 10 decibels is generally sufficient to result in what is perceived to be a significant reduction in the noise and is sufficient to reduce the offensive tone to the level of the other system noise sources. In FIGS. 3 and 4, the components are the same as those in FIGS. 1 and 2. Since a passive muffler 15 is generally used with this type of active source to eliminate the high frequency sound, the one-tenth wavelength rule will rarely be violated in practice.

There are several advantages to this orientation of active sources and the use of this type of source. First, the active anti-noise source can be located remotely from the hot exhaust pipe. This increases the potential that packaging solutions can be found, particularly on automobiles, in which the space limitations are severe. More importantly, though, the remote location of the active anti-noise source allows different materials to be used in the construction of the active anti-noise source to save weight, reduce cost and improve durability. For example, whereas the challenges of using plastic to construct the anti-noise source were severe when the source was in direct contact with the exhaust pipe, the use of plastic is a simple matter with the new outlet arrangement.

The active anti-noise source now can be disguised as a traditional "dual" exhaust package, which reduces the possibility consumers will react negatively to its appearance. The non-integral active muffler can now be placed within the vehicle's trunk if necessary and its use in what were near-impossible applications is now easier. For example, marine mufflers, in which a flow of water is mixed with the hot gases are now possible without exposing the active anti-noise source to water. The anti-noise source can be mounted above the waterline.

Figure 5:
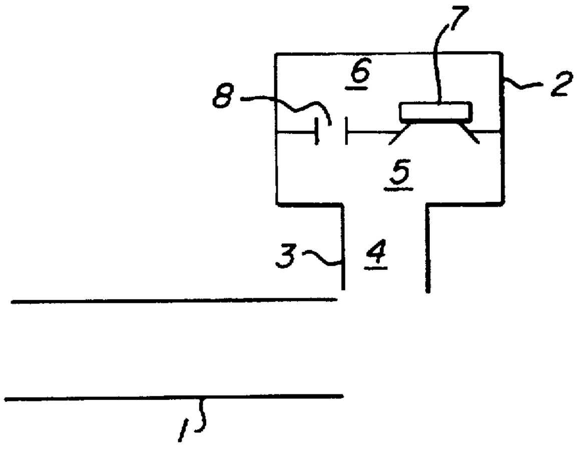
FIG. 5 shows another alternative embodiment of the muffler system of this invention.

One alternative arrangement is shown in FIG. 3 in which the non-integral active muffler outlet 1 is pointed 90 degrees away from the anti-noise source outlet 3 or in FIG. 5 where outlet pipe 1 and anti-noise source outlet 3 are place at a 90° angle from one another. In this manner, the acoustic centers of the two noise sources can be moved closer together to extend the upper frequency limit of the system. Other outlet arrangements and shapes are similarly possible and will be obvious to those skilled in the art.

Figure 6:
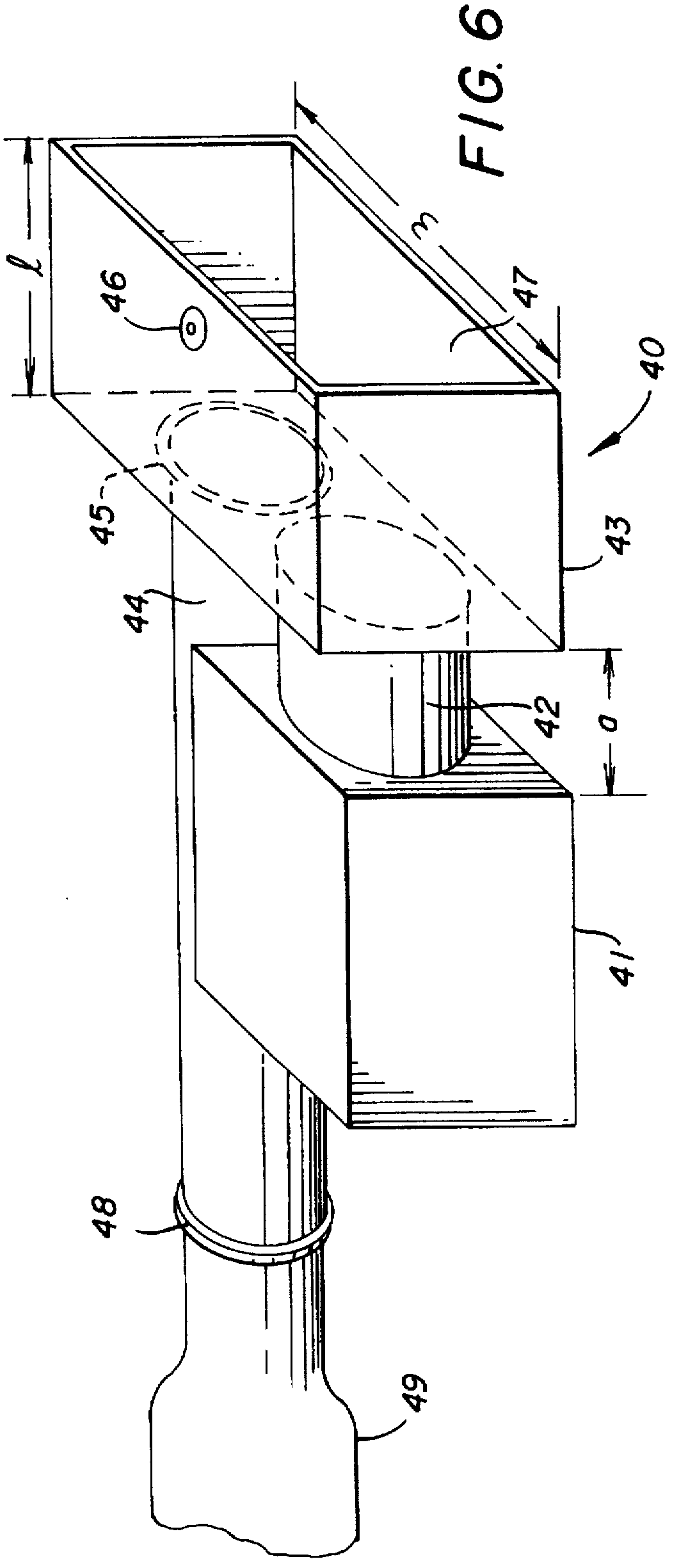
FIG. 6 is a perspective view of a fourth embodiment of the muffler system of this invention.

FIG. 6 shows the perspective of another alternative embodiment of this invention. The apparatus, generally denoted as 40 has a speaker enclosure (i.e., active enclosure) 41 which is connected via a connecting port 42 to duct extension 43. An opening, on the same side as the connecting port 42, in the duct extension 43 is adapted to receive the end of tail or exhaust pipe 44 and be secured thereto by an annular clamping means 45 which is similar to a pipe clamp. Connecting port 42 and tail pipe 44 enter duct extension 43 side by side so as to create dipole radiation of noise. The duct extension 43 alters and compresses this radiation into a plane wave which is sensed by a transducer listening device, which can be a microphone 46 as shown in the figure, as it exits an open end 47 of the duct extension 43. The tailpipe 44 is connected via a clamp 48 to a straight through muffler 49 which has very little flow resistance. The diameter of connecting port 42 is at least as large as the diameter of tailpipe 44.

The secondary source (active enclosure) 41 is a device similar to those mentioned above, but connected via connecting port 42, usually the same size or slightly larger than the exhaust pipe, to an extension duct. The behavior of this active enclosure 41 and the relationships between the various volumes and port sizes are generally dictated by the theory and response curves as discussed by A. N. Thiele, "Loudspeakers in Vented Boxes, Part 1", *Journal of the Audio Engineering Society*, March 1961, pp. 181–191 and Richard H. Small, "Closed-Box Loudspeaker Systems Part 11: Synthesis", *Journal of the Audio Engineering Society*, pp. 282–289. The extension duct 43 has several effects, all of which act to improve the performance of the system.

First, the duct extension 43 has the effect of coupling the noise from the exhaust pipe 44 and the anti-noise emitted from the active enclosure 41. The sound from these two sources, which are arranged as an acoustic dipole in one end of the extension, is combined and a plan wave exits the open end 47 of the duct extension 43.

Figure 11:
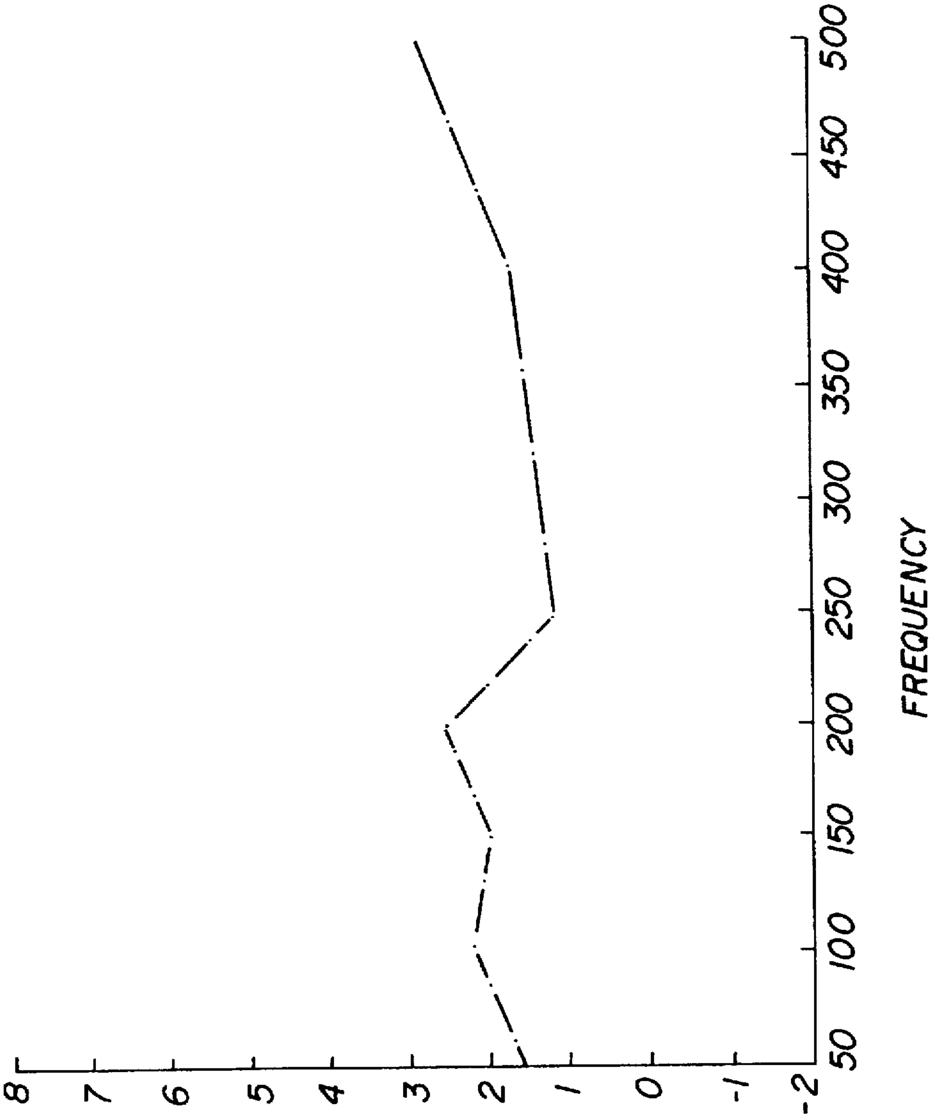
FIG. 11 is a plot of the reduction in drive voltage after adding an extension duct versus engine speed.

There are many secondary effects of using the extension duct 47. The larger the area of the duct extension 43 compared to the port of the active enclosure 41 increases the real part of the radiation impedance looking into the atmosphere. This impedance matching enables the active enclosure 41 to more efficiently radiate sound into the atmosphere, which results in decreased power consumption. This is critical in an automotive application, in which size and power consumption must be kept to a minimum. FIG. 11 shows the reduction in drive voltage when adding an extension duct 43 to an existing active muffler. The shape and area of the extension should be larger than the combined areas of the port to the active muffler and the exhaust pipe, but the dimensions must be only large enough to keep the cut-on frequency (frequency at which acoustical waves propagate across the device instead of just above its axis) of non-plane wave behavior in the extension above the operating frequency range. For a rectangular extension, this means the maximum dimension perpendicular to the axis of the duct 2w, must be less than c/2f where c is the speed of sound and f is the maximum operating frequency. For a circular extension, the diameter must be less than $1.841c/\pi f$. The length of the extension should be no more than one quarter wave length of the maximum operating frequency, and preferably greater than the smallest extension cross sectional dimension. The exact shape of the extension is not critical and various shapes and end formats, such as beveling, can be used to achieve the styling objectives for the vehicle without affecting performance.

Figure 13:
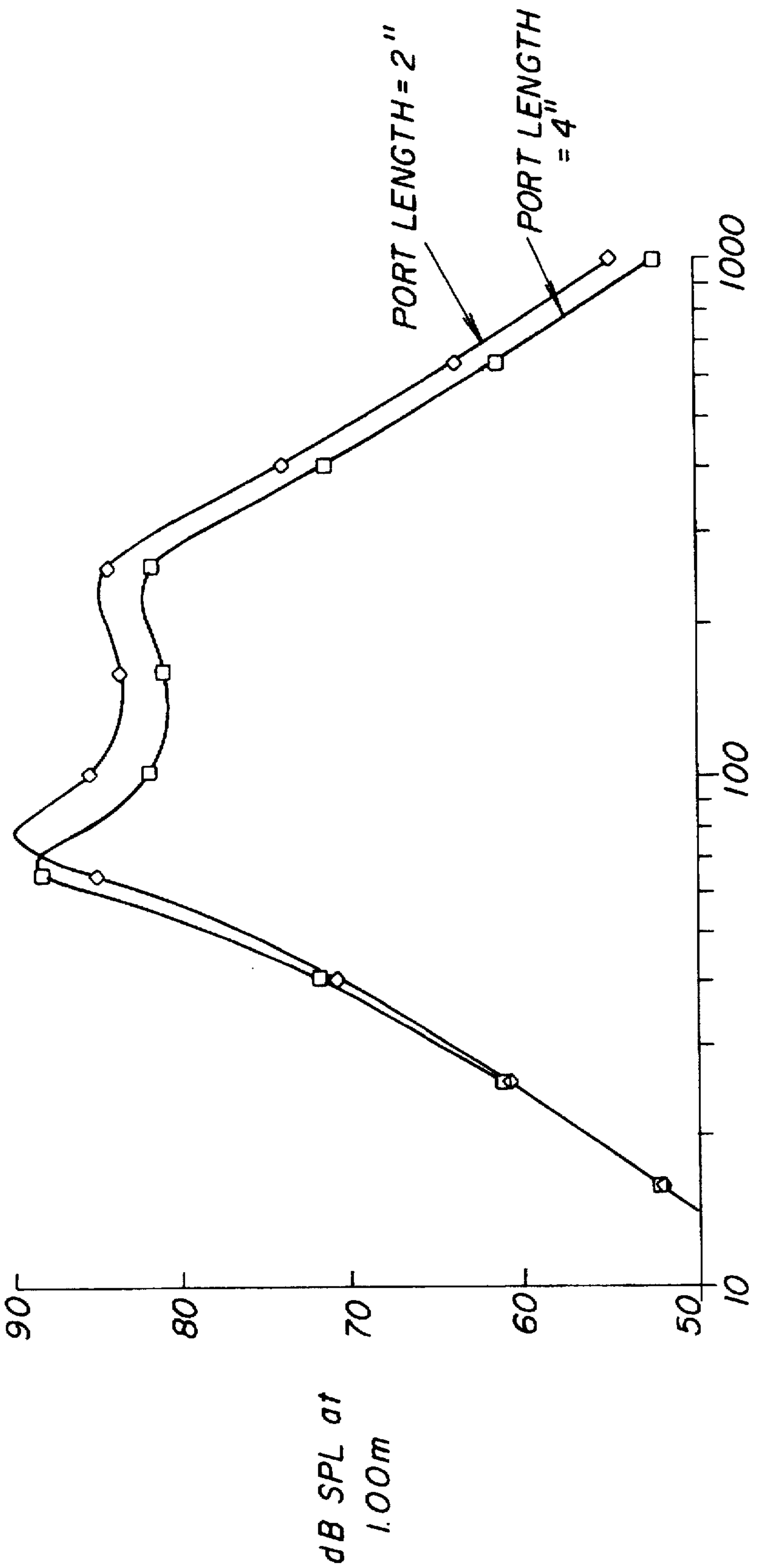
FIG. 13 is a plot of active muffler output with different output port lengths.

The extension duct is used to channel harmful exhaust fumes and allows the fumes to exit from underneath the car at the regulatory distance. This feature enables the active muffler to be positioned farther underneath the car, yet still have a shorter port leading into the extension duct. The effect of this reduction in port length is shown in FIG. 13, in which the response of an active muffler to a one volt input at a distance of one meter is shown for different length ports.

The extension duct cross sectional area is large enough that the pressure within the extension is essentially atmospheric or slightly below because of the abrupt expansion. This prevents any exhaust gases from being forced into the active muffler enclosure, and the slight vacuum can even be used to pull cooling air into the active enclosure if this is desired.

Figure 12:
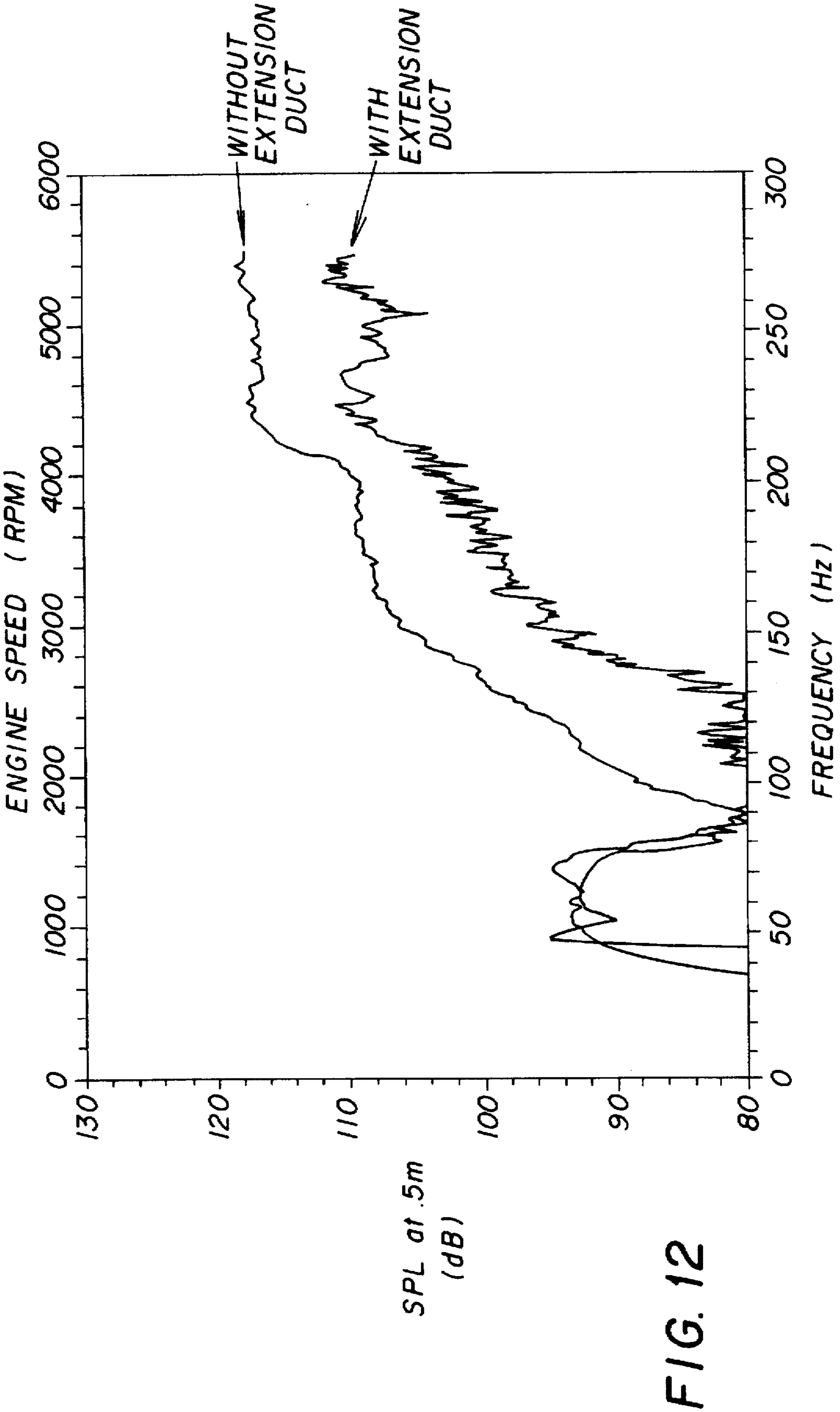
FIG. 12 is a plot of acoustic output with and without an extension duct versus engine speed.

The fact that a plane wave is now exiting the extension duct makes the placement of the error sensing microphone less critical since a plane wave source in a duct results in a less directive radiation pattern than an acoustic dipole, There is now no reason to use more than one error sensing microphone. This and the improved coupling between the two sources produce a marked performance improvement as shown in FIG. 12. The reduction in exhaust noise is significantly improved from just adding the extension duct. The sensing microphone measures the resultant noise at the end of the system and the adaptive controller rapidly adjusts its output at a single frequency or at hundreds of frequencies continuously and automatically to achieve nearly total noise cancellation as discussed in detail in the documents incorporated by reference.

The dimensions of the cross-sectional area of duct extension 43 are such that the frequency at which non-plane wave behavior or propagation begins is above the operating frequency of the controller as discussed above and its length is at least as large as the minimum dimension of the extension perpendicular to its axis, and shorter than a quarter of a sound wavelength at the highest frequency to be controlled. This requirement can be stated as length, $l<c/4f$.

Figure 7:
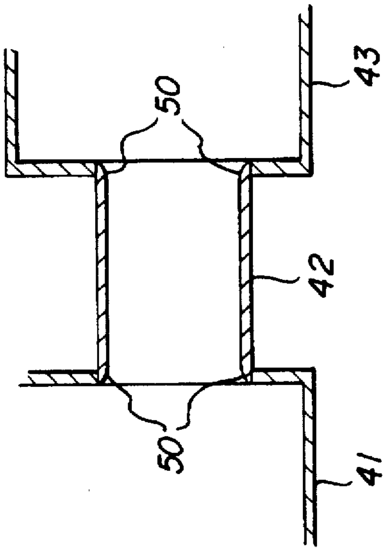
FIG. 7 is a cross-sectional view of the port connection of FIG. 6.

FIG. 7 shows the inside of port 42 to be flared as at 50 to reduce flow turbulence.

Figure 8:
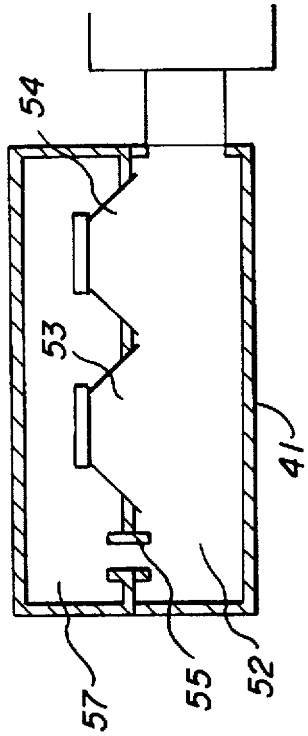
FIG. 8 is a cross-sectional view of the speaker enclosure of FIG. 6.

FIG. 8 shows a cross-sectional view of speaker enclosure 41 with rear cavity 51, front cavity 52 and speaker 53. If required, a second speaker 54 may be added. A port 55 may also be provided to make the arrangement behave as a 6th order speaker as described in PCT/US91/02731 and herein incorporated by reference.

Figure 9:
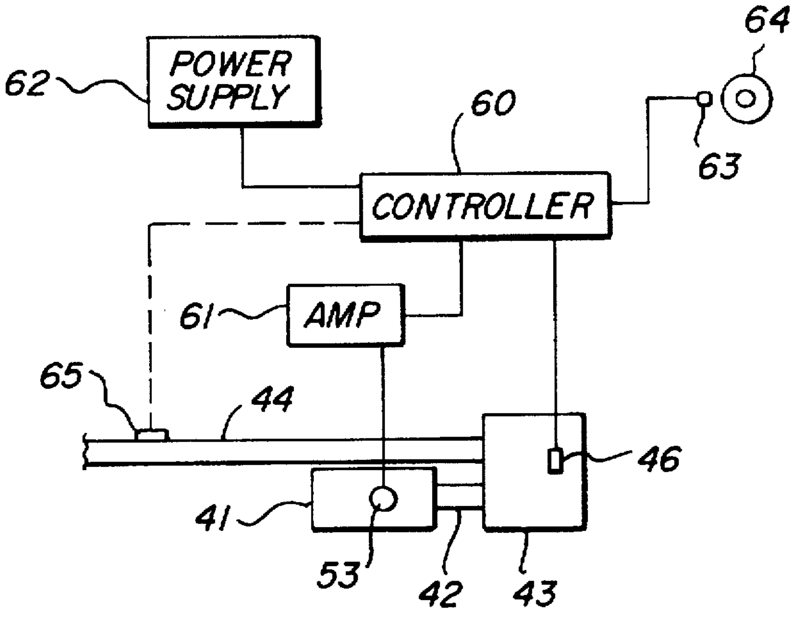
FIG. 9 is a block diagram of the control system.

The control system is shown generally in FIG. 9 with controller 60 and amplifier 61 driving speaker 53 in enclosure 41. Power supply 62 is connected to controller 60 as is residual microphone 46. If the system is using only a residual microphone a sync connection 63 to an engine flywheel 64 or the like is necessary. If no sync is used a digital virtual earth or an adaptive feedforward system with an upstream sensing microphone 65 can be used.

Figure 10:
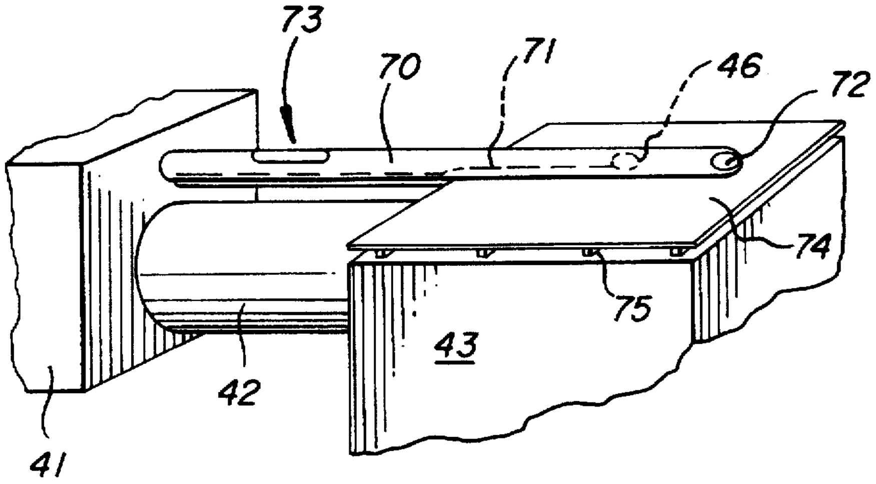
FIG. 10 is a partial perspective view of a heat shield/air vent/cable conduit.

FIG. 10 shows a combination hollow heat shield and conduit unit 70 mounted atop duct extension 43 and containing a cable 71 to microphone 46, enclosed by 70 which also has vent holes 72, 73 to allow outside air to ingress and egress to cool microphone 46. The unit also protects microphone 46 from road debris and the like. The conduit unit 70 may be mounted on heat shield 74 which is held in a spaced relationship to duct 43 by spacers 75. This allows for further heat relief of microphone 46. Conduit 70 has two passageways, one for the cooling air and one for the cable 71.

This invention utilizes the significant advantages gained by applying an extension duct of particular dimension to the source and counter noise to overcome the practical problems of cost, durability, efficiency, regulatory requirements and appearance involved in putting such a counter noise device into commercial use.

This invention allows designers to use commercially available components because the invention avoids exposing its counter noise component to hot, corrosive gases, and high exhaust system pressures. Thus, the invention has low cost and high durability.

Of course, it should be understood that a wide range of changes and modifications can be made to the preferred embodiments described above. It is therefore intended that the foregoing detailed description be regarded as illustrative rather than limiting, and that it is the following claims, including all equivalents, which are intended to define the scope of the invention.

We claim:

1. An active noise canceling muffler system for use on stationary or vehicle applications which involve an exhaust pipe, said system comprising:

an active noise enclosure:

an active noise attenuator in said active enclosure adapted to produce a counter noise wave to cause destructive interference with a noise wave emanating from said exhaust pipe;

an adaptive controller connected to said active noise attenuator;

an extension duct connected to said active enclosure through a port and adapted to receive a terminus of said exhaust pipe so as to receive both said exhaust pipe gases, said noise and said counter noise at one end of said extension duct, said noise and counter noise combining to form a single plane wave at an opposite end of said extension duct; and a transducer listening device on said extension duct and adapted to provide a residual signal to said adaptive controller to allow it to adjust said active noise attenuator to provide the necessary counter noise, wherein a dipole is created where the noise and counter noise enter said duct extension, the shape of said duct extension forcing said dipole pattern into a plane wave adjacent said transducer listening device.

2. A system as in claim 1 wherein said port has generally the same cross-sectional area or larger than said exhaust pipe.

3. A system as in claim 1 wherein said port is relatively short in length so as to reduce the acoustic mass and increase the efficiency of said muffler.

4. An active noise canceling muffler system for use on stationary or vehicle applications which involve an exhaust pipe, said system comprising:

an active noise enclosure;

an active noise attenuator in said active enclosure adapted to produce a counter noise wave to cause destructive interference with a noise wave emanating from said exhaust pipe;

an adaptive controller connected to said active noise attenuator;

an extension duct connected to said active enclosure through a port and adapted to receive a terminus of said exhaust pipe so as to receive both said exhaust pipe gases, said noise and said counter noise at one end of said extension duct, said noise and counter noise combining to form a single plane wave at an opposite end of said extension duct; and a transducer listening device on said extension duct and adapted to provide a residual signal to said adaptive controller to allow it to adjust said active noise attenuator to provide the necessary counter noise, wherein the length of the extension duct is larger than the smallest cross section dimension, but less than one fourth of a wavelength of sound at the maximum frequency controlled.

5. A system as in claim 1 or 4 including a heat shield to keep said transducer listening device from the hot exhaust gases flowing through said duct extension.

6. A system as in claim 5 wherein said heat shield includes an outside air flow vents.

7. A system as in claim 1 or 4 wherein said active noise attenuator includes a closed back cavity, a front cavity in communication with said duct extension means and a speaker means between said front and back cavities and is adapted to produce counter noise into said front cavity.

8. A system as in claim 1 or 4 wherein said adaptive controller includes a synchronization means adapted to sync the control cycle to the cycle of a unit producing the exhaust gases and noise.

9. A system as in claim 1 or 4 and including a second transducing listening device adapted to be placed upstream on said exhaust pipe so as to provide a first signal to said adaptive controller.

10. A system as in claim 9 wherein both of said transducing listening devices are microphones.

11. A system as in claim 1 or 4 wherein said enclosure is constructed of plastic.

12. A system as in claim 1 in which the cross-sectional area of the extension duct is of arbitrary shape but at least as large as the cross sectional area of the port and the exhaust pipe combined, and the largest dimension of a rectangular-shaped extension duct in the direction perpendicular to the axis of the extension is not larger than $c/2f$, where c is the speed of sound and f is the highest frequency to be controlled.

13. A system as in claim 1 in which the cross-sectional area of the extension duct is of arbitrary shape but at least as large as the cross sectional area of the port and the exhaust pipe combined, and the largest dimension of a circular-shaped extension duct in the direction perpendicular to the axis of the extension is not larger than $1.841c/\pi f$, where c is the speed of sound and f is the highest frequency to be controlled.

* * * * *